(12) United States Patent
Wang

(10) Patent No.: US 7,009,188 B2
(45) Date of Patent: Mar. 7, 2006

(54) LIFT-OUT PROBE HAVING AN EXTENSION TIP, METHODS OF MAKING AND USING, AND ANALYTICAL INSTRUMENTS EMPLOYING SAME

(75) Inventor: Shixin Wang, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 10/838,878

(22) Filed: May 4, 2004

(65) Prior Publication Data

US 2005/0247886 A1 Nov. 10, 2005

(51) Int. Cl.
G21K 5/10 (2006.01)
G01N 35/10 (2006.01)
H01J 37/08 (2006.01)
H01J 37/20 (2006.01)

(52) U.S. Cl. .............. 250/442.11; 250/307; 250/492.1; 250/492.3; 438/464

(58) Field of Classification Search ................ 250/304, 250/306, 307, 309, 398, 400, 548, 559.19, 250/559.27, 559.3, 492.1–3, 492.21–23, 250/442.11; 438/464, 758, 765; 216/2, 216/38
See application file for complete search history.

(56) References Cited

U.S. PATENT DOCUMENTS

| | | | | |
|---|---|---|---|---|
| 5,441,343 A | * | 8/1995 | Pylkki et al. | 374/137 |
| 5,485,536 A | * | 1/1996 | Islam | 385/31 |
| 5,664,036 A | * | 9/1997 | Islam | 385/31 |
| 5,703,366 A | * | 12/1997 | Sting et al. | 250/341.2 |
| 6,188,068 B1 | * | 2/2001 | Shaapur et al. | 250/307 |
| 6,188,072 B1 | | 2/2001 | Chung | |
| 6,420,722 B1 | | 7/2002 | Moore et al. | |
| 6,570,170 B1 | | 5/2003 | Moore | |
| 6,576,900 B1 | | 6/2003 | Kelly et al. | |
| 6,777,674 B1 | * | 8/2004 | Moore et al. | 250/307 |
| 6,841,788 B1 | * | 1/2005 | Robinson et al. | 250/492.3 |
| 2002/0079463 A1 | | 6/2002 | Shichi et al. | |
| 2002/0121614 A1 | * | 9/2002 | Moore | 250/492.1 |
| 2002/0166976 A1 | | 11/2002 | Sugaya et al. | |
| 2004/0056194 A1 | * | 3/2004 | Moore et al. | 250/307 |

OTHER PUBLICATIONS

Omniprobe Information Sheet, Omniprobe webpage, 1 page.
Fibics Incorporated webpage http://www.fibics.com, "Fibics Semiconductor TEM Specimens Prepared by "Lift-out" Method", 18 pages.
Roberts et al., "FIB-TEM sample preparation by in-situ lift-out technique", Philips Semiconductors Nijmegen PMO, 24 pages.
LEO 1560 Cross Beam, Applications Overview, 37 pages.

* cited by examiner

Primary Examiner—John R. Lee
Assistant Examiner—Bernard E. Souw
(74) Attorney, Agent, or Firm—TraskBritt

(57) ABSTRACT

Extension tips for lift-out probes used in conjunction with focused ion beam (FIB) systems and analytical instruments employing such probes are disclosed. Methods of forming the extension tips from a variety of materials such as a silicon wafer, preformed whiskers of conductive material, and metal lines or contacts removed from integrated circuits are also disclosed. Methods of using a variety of extension tips pre-placed within the FIB system to enable reconditioning worn or damaged lift-out probes are also disclosed.

38 Claims, 7 Drawing Sheets

LIFT-OUT PROBE HAVING AN EXTENSION TIP, METHODS OF MAKING AND USING, AND ANALYTICAL INSTRUMENTS EMPLOYING SAME

BACKGROUND OF THE INVENTION

1. Field of the Invention

The present invention relates to lift-out probes used in conjunction with a focused ion beam system. More specifically, the present invention relates to modifying an existing lift-out probe to provide an extension tip having a small tip diameter.

2. State of the Art

Focused ion beam (FIB) systems, which may include imaging capability using focused ion beam microscopy and scanning electron microscopy (SEM), are used extensively in failure analysis of semiconductor devices and for the preparation of electron-transparent specimens for transmission electron microscopy (TEM). The FIB lift-out technique is a commonly used procedure in which a small piece of sample is cut from a larger bulk sample, such as a silicon wafer containing integrated circuits, using a focused ion beam. After the sample has been ion milled, a lift-out probe, typically formed from a metal such as tungsten is contacted with the ion milled sample using a controller that is operably coupled to the FIB system. An organometallic gas flow is introduced through a tube that accesses the chamber that the sample is located in and an ion beam hits the organometallic gas at the interface between the lift-out probe and the sample to bond them together by deposition of a metal constituent of the gas. The ion milled sample may then be moved to another sample support for further analysis or processing by appropriate positioning of the lift-out probe with the sample attached thereto. The lift-out probe is then debonded from the sample by ion milling with the FIB. In the case of analysis using TEM, further ion milling to thin the sample to a suitable thickness is needed. Once the ion milled samples that have been removed from the larger samples have been thinned to an appropriate thickness, the sample may be analyzed using TEM.

The above process for removing samples using the FIB system and a lift-out probe is effective for preparing TEM samples. Commercially available lift-out probes, such as those available from Omniprobe, Inc., of Dallas, Tex., initially have a tip radius of as small as 0.1 $\mu$m and a 325 $\mu$m taper length. However, repeated use of the lift-out probes to contact samples and bond to samples, results in wear and damage to the probe tip. The lift-out probes are often worn prematurely to such an extent that the tip diameter is too large to effectively contact and be bonded to desirably small samples. This wear is partly due to the metal deposition onto the probe tip, but is also a result of having to cut a portion of the lift-out probe to sever it from the sample to which it is bonded with each use.

Once the tip diameter of a used lift-out probe is worn to around 10 $\mu$m, only larger samples can be lifted-out, or removed, from the larger bulk sample. This requirement subsequently results in longer ion milling times to produce TEM specimens. Furthermore, a larger lift-out probe is also more difficult to control and handle small specimens, such as TEM-ready samples of about 100 nm thickness. In addition, a larger, worn probe tip blocks the view of a location of interest on the larger bulk sample, and is more likely to cause damage to the sample.

Accordingly, there is a need for a practical technique to recondition used lift-out probes to provide small diameter probe tips suitable for effecting the lift-out of small ion milled specimens. Fulfilling this need would significantly reduce, if not eliminate, the need for replacement of the costly lift-out probes employed in FIB systems.

BRIEF SUMMARY OF THE INVENTION

The present invention, in a number of embodiments, includes probe structures for use in focused ion beam (FIB) systems for lifting-out, or removing, specimens from larger bulk samples and analytical instruments that employ such probes. Methods for fabricating and using the inventive probe structures are also disclosed. The probe structures of the present invention may include a probe member in the form of a conventional lift-out probe having at least one extension tip bonded thereto. The lift-out probe to which the extension tip is bonded may be worn or have been broken several times during use such that it no longer possesses a tip diameter small enough to effectively remove desirably small specimens from a larger bulk sample. Thus, the present invention provides a technique for extending the useful life of a lift-out probe.

The probes of the present invention facilitate the extraction of smaller specimens from a larger bulk sample, such as an integrated circuit, using a FIB system. The specimens may be further examined using FIB microscopy, scanning electron microscopy (SEM), transmission electron microscopy (TEM), or another analytical technique. Such examination is important for failure analysis of semiconductor-based electronic structures and, in particular, integrated circuits, such as are employed in semiconductor memory devices.

In one aspect of the present invention, a probe structure is disclosed. The probe structure may include an elongated probe member in the form of a lift-out probe sized and configured to access a chamber of a FIB system. A base, or proximal portion of an elongated extension tip may be coupled to a front end region of the lift-out probe. If desired, the probe structures of the present invention may employ multiple extension tips, of the same or increasingly smaller size, sequentially longitudinally bonded to one another and extending distally from the end region of the lift-out probe.

In another aspect of the present invention, an analytical instrument is disclosed. The analytical instrument includes a focused ion beam system and a micromanipulator system. The micromanipulator system includes a probe controller that controls a probe structure of the present invention to access a chamber of the focused ion beam system.

In another aspect of the present invention, a method of fabricating a probe structure is disclosed. A lift-out probe comprising an elongated probe member that comprises a front end region defined by at least one lateral dimension and a back end region is provided. A proximal portion of a body having a smaller lateral dimension than the front end region of the probe member may be relatively positioned to contact the front end region of the lift-out probe. The front end region of the probe member may be bonded to the proximal portion of the body to form an extension tip. The portion of the body bonded to the probe member may be severed from the remainder of the body to form the extension tip, or the body may be a preformed body of a desired size and shape for an extension tip. If necessary or desirable, a focused ion beam may be used to ion mill the body portion bonded to the probe member after severance to a desired size and shape.

In yet another aspect of the present invention, a method of selectively fabricating and reconfiguring a probe structure is disclosed. A plurality of preformed extension tips of predetermined size and shape, each having a proximal portion and a distal portion, are provided inside a focused ion beam chamber. A selected extension tip of the plurality of extension tips may be oriented relative to a probe member comprising a lift-out probe. A front end region of the lift-out probe may be bonded to the proximal portion of the selected extension tip. The selected extension tip may be severed from the end of the lift-out probe, and another selected extension tip bonded thereto. Thus, extension tips may be replaced as they become worn, or differently sized and shaped extension tips added to the lift-out probe. A plurality of extension tips of ever-smaller dimensions may be sequentially bonded to the front end region of the lift-out probe and to the next previously bonded extension tip.

In a further aspect of the present invention, methods of use of the probe structures of the present invention are also encompassed thereby.

These features, advantages, and alternative aspects of the present invention will be apparent to those of ordinary skill in the art from a consideration of the following detailed description taken in conjunction with the accompanying drawings.

BRIEF DESCRIPTION OF THE SEVERAL VIEWS OF THE DRAWINGS

In the drawings, which illustrate what is currently considered to be the best mode for carrying out the invention.

DETAILED DESCRIPTION OF THE INVENTION

The present invention, in a number of embodiments, includes probe structures for use in removing minute specimens from larger bulk samples, and analytical instruments employing such probes. Methods of making and using the probes are also disclosed. The probes of the present invention may comprise, in part, elongated probe members comprising conventional lift-out probes as used in focused ion beam (FIB) systems modified by bonding at least one extension tip thereto. The extension tip provides a smaller tip diameter than the lift-out probe to which it is bonded, and a plurality of progressively smaller extension tips may be bonded to one another extending outwardly from the end of the probe member. The lift-out probe to which the extension tip is bonded is typically worn or has been broken several times during use such that it no longer possesses a tip diameter small enough to effectively remove desirably small specimens from a larger bulk sample for examination. The present invention also includes methods of fabricating the probes and employing the probes for SEM and TEM specimen preparation. The probes of the present invention facilitate the extraction of smaller specimens from a larger bulk sample, such as an integrated circuit, using a FIB system, to be further examined using FIB microscopy, SEM, or TEM. Such examination is an important tool for failure analysis of semiconductor devices, in-line SEM and TEM analysis of semiconductor devices, and structural analysis of processed semiconductor devices on wafers.

Figure 1:
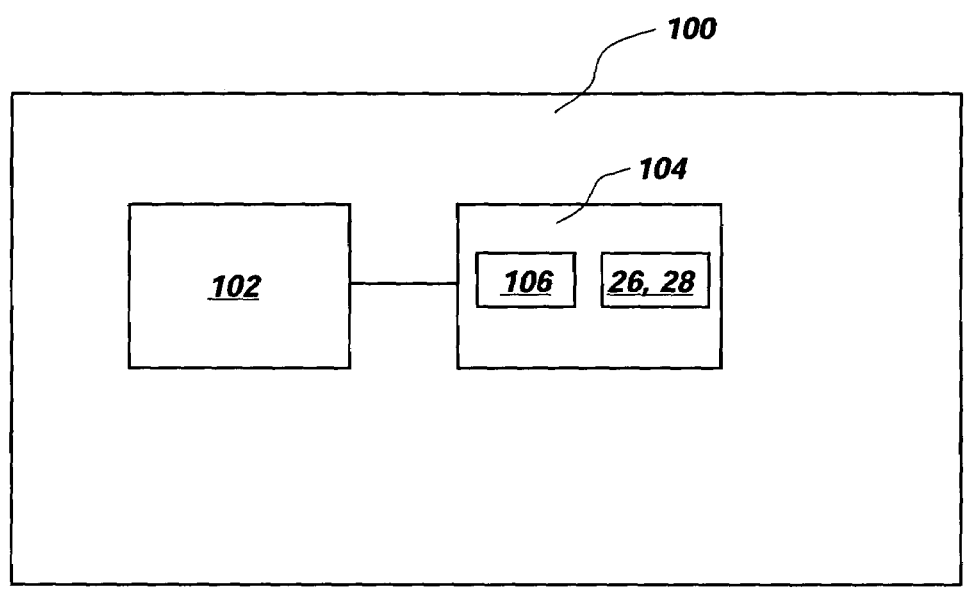
FIG. 1 depicts a block diagram of an exemplary analytic instrument comprising a focused ion beam system and a micromanipulator system that employs a probe according to the present invention.

In general, lift-out probes are part of a commercially available micromanipulator system as employed by many FIB systems. Referring to FIG. 1, an exemplary analytical instrument 100 that employs the probes of the present invention is depicted using a simplified block diagram. The analytical instrument 100 includes a FIB system 102. Suitable FIB systems that may be employed to practice the present invention are commercially available from FEI Company of Hilsboro, Oreg. Such FIB systems enable ion milling multiple samples with a focused ion beam and have the capability to image the samples using either a focused ion beam microscopy or a SEM. A micromanipulator system 104 may be employed to manipulate a sample taken from a workpiece, such as a semiconductor wafer, inside a chamber of the FIB system 102 in a controlled manner. The micromanipulator system 104 includes a probe controller 106 to which a probe structure or "probe" 26 or "probe" 28 of the present invention is operably coupled. One suitable micromanipulator system 104 that may be employed to practice the present invention is the Omniprobe Autoprobe commercially available from Omniprobe, Inc., of Dallas, Tex. The probe controller 106 enables the user of the analytical instrument 100 to accurately position the probe 26 or the probe 28 on a desired location of the workpiece to retrieve a sample while, if desired, imaging the sample location on the workpiece using field ion beam microscopy or an electron microscopy technique.

Figure 2A:
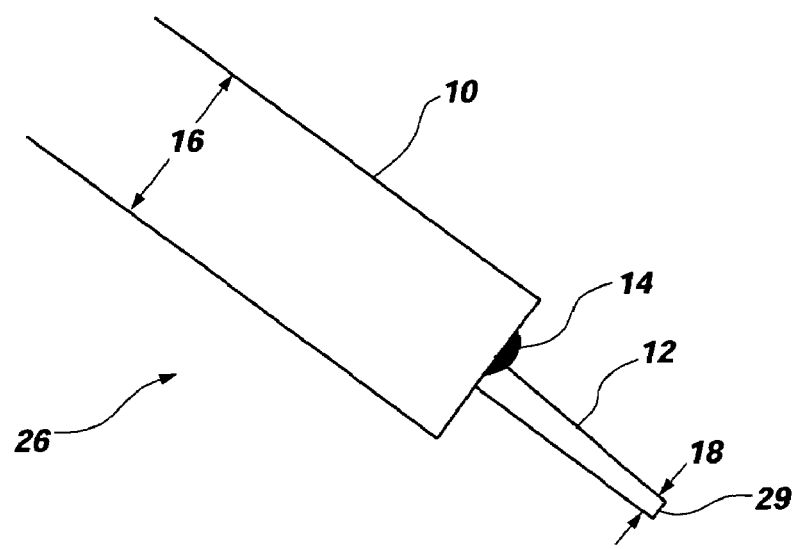
FIGS. 2A and 2B are illustrations of a lift-out probe having an extension tip bonded thereto.
Figure 2B:
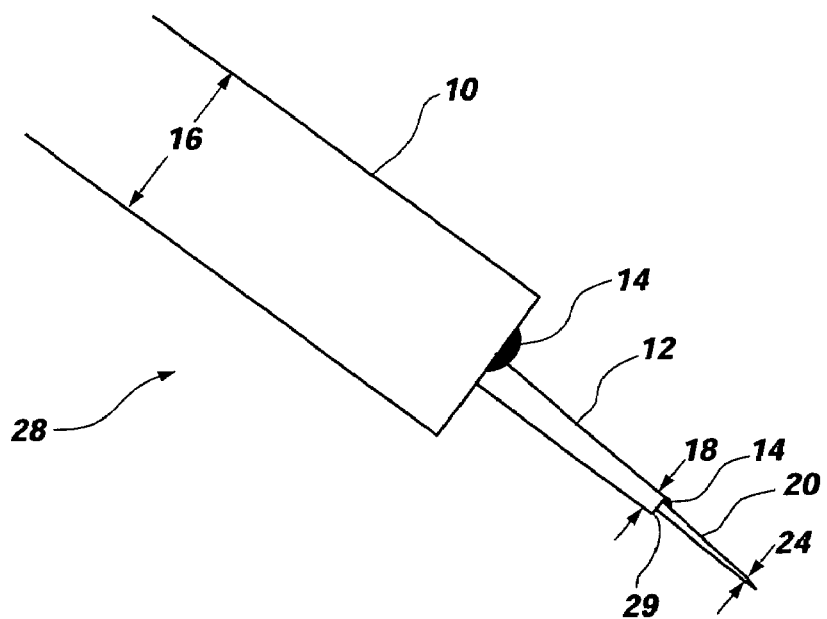

The configurations of two exemplary embodiments for the probe structures of the present invention are illustrated in FIGS. 2A and 2B. Referring to FIG. 2A, a conventional elongated lift-out probe 10 is shown having an elongated extension tip 12 bonded thereto. The conventional lift-probe 10 may be a probe such as the aforementioned lift-out probes commercially available from Omniprobe, Inc. of Dallas, Tex. Lift-out probe 10 may be formed from a material such as tungsten or another metal or alloy. The lift-out probe 10 may have bonded thereto an extension tip 12 having a smaller lateral dimension than lift-out probe 10. Extension tip 12 may be formed from any conductive material such as metals (e.g., copper, gold, silver), alloys thereof, or semiconductor materials (e.g., silicon, germanium, and gallium arsenide). The extension tip 12 may be bonded to the lift-out probe 10 using a bonding constituent 14, such as a metal or an alloy, which is deposited in a localized area to affix an end of the extension tip 12 to an end of the lift-out probe 10. In the case of using a metal for the bonding constituent 14, the metal may be deposited using a chemical vapor deposition technique that will be discussed in more detail below. FIG. 2B illustrates another exemplary embodiment that further includes another extension tip 20 that exhibits a smaller diameter than the extension tip 12 and is bonded to the distal end thereof. The extension tip 20 may be bonded to the extension tip 12 using the bonding constituent 14. Although only one additional extension tip 20 is shown in FIG. 2B, one or more additional extension tips may be sequentially bonded to extension tip 20 to form a longer probe. If the probe 26 or the probe 28 of the present invention is used in a SEM that is part of a FIB system, such as FIB system 102, extension tips 12, 20, as well as any other extension tip employed, should be formed from a conductive material to prevent charge build-up around the extension tip during use in a SEM.

Lift-out probe 10 and extension tips 12 and 20 are illustrated in FIGS. 2A and 2B as having a uniform diameter; however, it should be understood that they may have a distally tapering cross-section, a non-circular cross-section, or both. Representative dimensions for the lift-out probe 10 are a diameter 16 of about 10 $\mu$m and a length of about 325 $\mu$m. Suitable dimensions for the diameter or lateral extent 18 of the extension tip 12 near its distal end 29 may be about 0.1 $\mu$m to about 2 $\mu$m. An exemplary distal end tip diameter for extension tips 12 and 20 is about 20 nm. It is desirable for lift-out probe applications that the length of the extension tip 12 be greater than about 1 $\mu$m and may be about 10 $\mu$m to 30 $\mu$m. Referring to FIG. 2B, the extension tip 20 exhibits a smaller distal end diameter or lateral dimension 24 than that of the extension tip 12 to which it is bonded. The above dimensions are merely illustrative and other dimensions may be used for extension tips of probes of the present invention, as long as they are suitably sized for use in a chamber, such as those employed in a FIB system, and are sufficiently mechanically stable for their intended use, such as sample retrieval.

Figure 3A:
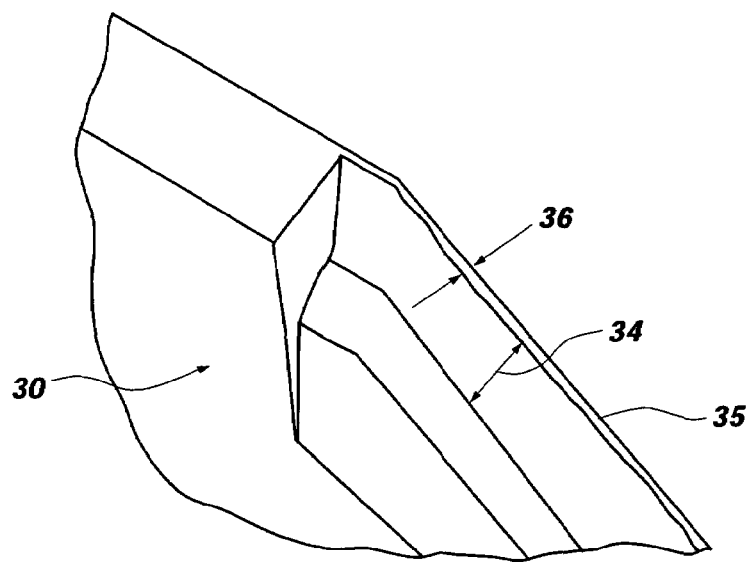
FIGS. 3A–3D are illustrations of an exemplary method for fabricating an extension tip from a silicon wafer.
Figure 3B:
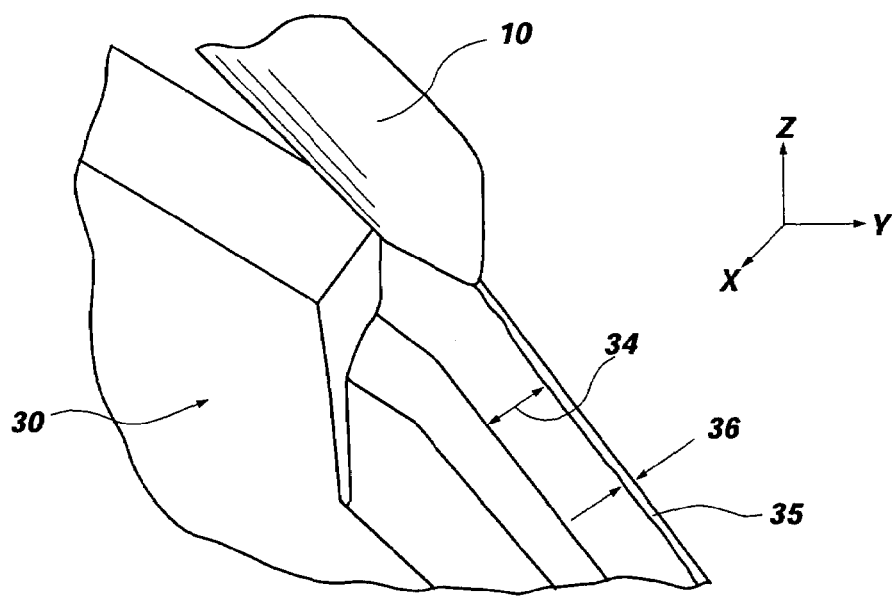
Figure 3C:
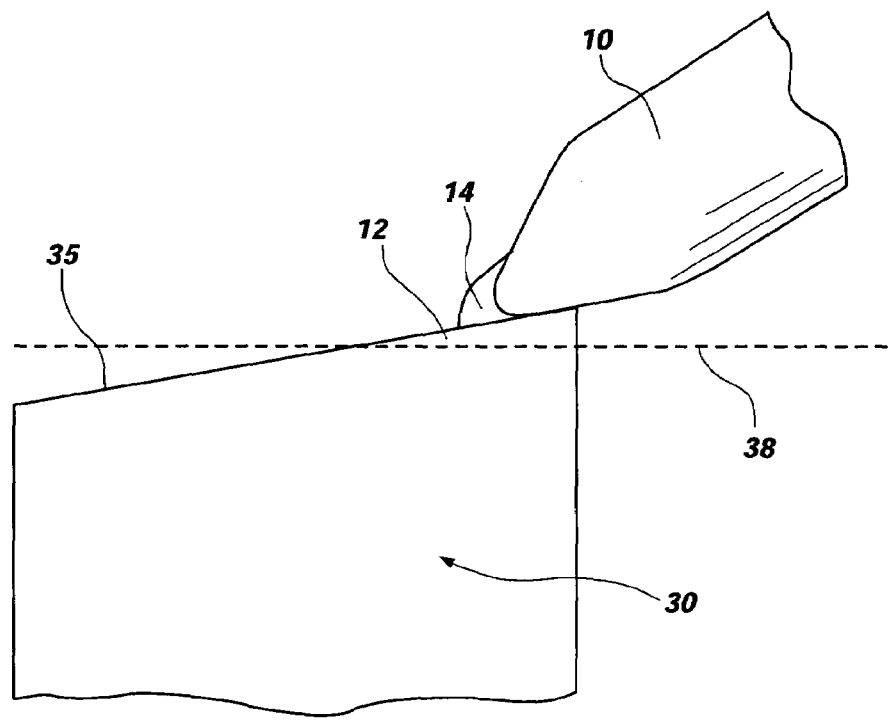

An exemplary method for forming the the probe 26 and the probe 28, of the present invention, is described in detail with respect to FIGS. 3A–3C. A fractured silicon piece is mounted on a sample support (not shown) inside a chamber of a FIB system. The fractured silicon piece is suitably sized to fit inside the chamber of the FIB system. The fractured silicon piece may be formed by fracturing a thinned silicon wafer ground to a thickness of about 5 $\mu$m using an instrument such as a razor or tweezers to produce an angled corner. As depicted in FIG. 3A, a portion of the angled corner of the fractured silicon piece may be further thinned to the desired dimensions and geometry by FIB milling to form a thinned silicon piece 30 having an edge 35 exhibiting a thickness 36 of about 2 $\mu$m and a corner region having a depth 34 of about 4 $\mu$m. The length of the edge 35 having the thickness 36 may be greater than about 30 $\mu$m. As discussed in more detail below, an extension tip 12 or 20 will be formed from a portion of the thinned silicon piece 30 having the edge 35. While a fractured piece of single crystal silicon is employed in the exemplary example shown in FIGS. 3A–3C, single crystal germanium, single crystal gallium arsenide, or another suitable semiconductor substrate may also be used.

As shown in FIG. 3B, the lift-out probe 10 may be moved into position using the probe controller 106 (FIG. 1) to contact the edge 35 of the thinned silicon piece 30. The lift-out probe 10 is typically fixed at a specific angle in commercially available micromanipulator systems. This angle is usually about 45° with respect to the vertical, but the precise probe angle depends on the particular micromanipulator system manufacturer. The sample support may be selectively translated in X, Y, and Z directions and be selectively angularly rotated about the X, Y and Z axes. Thus, the thinned silicon piece 30 and the lift-out probe 10 may be relatively oriented to a desired orientation and position with respect to each other, such that the length of the lift-out probe 10 and the edge 35 having the thickness 36 may be substantially aligned and placed in contact with one another. The edge 35 having the thickness 36 of the thinned silicon piece 30 may, for example, be oriented at about 45° relative to the plane of the sample support.

Figure 3D:
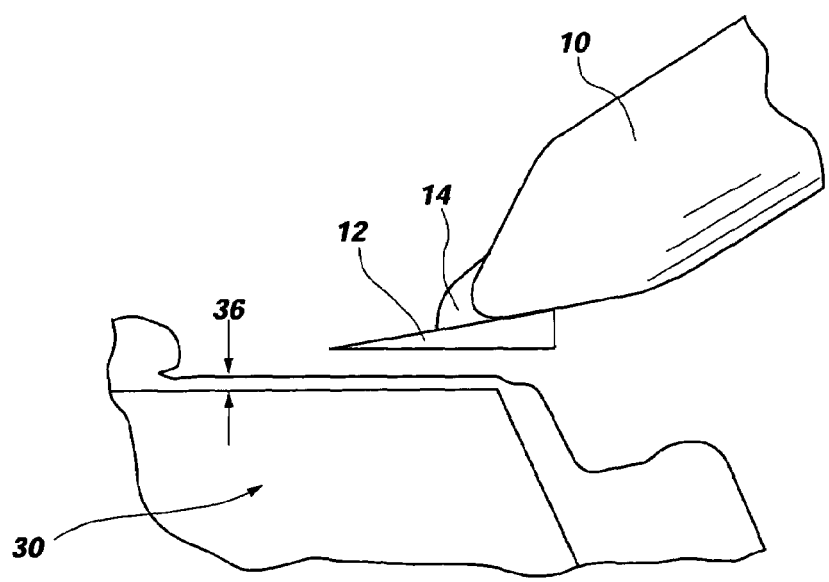

Referring to FIG. 3C, a view of the opposite side of the thinned silicon piece 30 is shown. An organometallic gas containing platinum may be applied, at least proximate an interface between the edge 35 of the thinned silicon piece 30 and the lift-out probe 10, using a gas injection system (GIS) provided with most commercially available FIB systems. The GIS may apply the organometallic gas through a tube that is operably coupled to a controller of the FIB system 102 (FIG. 1). Once the desired gas has been applied, a controlled FIB (having a spot size as small as 8 nm) may be used to hit the gas in the region proximate the interface of the end of the lift-out probe 10 with the edge 35 of the thinned silicon piece 30 to cause metal deposition from the organometallic gas to bond (shown as bonding constituent 14) the edge 35 to the end of the lift-out probe 10. Depending on the specific type of organometallic gas, the FIB hitting the organometallic gas causes a metal from the organometallic gas, such as platinum or tungsten, to be deposited and to bond the lift-out probe 10 to the edge 35 of the thinned silicon piece 30. Then, the FIB may be used to remove a sliver-shaped portion of the thinned silicon piece 30 bonded to the lift-out probe 10 to form the extension tip 12 of the probe 26 (FIG. 2A) by ion milling using a controlled FIB along a line 38. As shown in FIG. 3C, the extension tip 12 may be formed by traversing the FIB along a selected path to sever a portion of the thinned silicon piece 30 bonded to lift-out probe 10 by ion milling along line 38 to form an angular extension tip 12 having a small tip diameter bonded to the lift-out probe 10. As depicted by FIG. 3D, the length of the extension tip 12 formed may be about 28 $\mu$m and the tip diameter may be on the order of 20 nm. Such a fine tip diameter for extension tip 12 enables removing extremely small specimens from a larger bulk sample. The fine tip diameter of extension tip 12 facilitates application of the tip in a small, specific location of a sample with less of a chance of causing mechanical damage to the sample. Extension tip 12 may be further micromachined by FIB milling as desired after severance by ion milling.

The foregoing process may be repeated to form an additional extension tip 20 bonded to extension tip 12, as shown in FIG. 2B. As noted above, additional extension tips may likewise be added by sequential bonding.

Although an extension tip may be formed of a thinned, fractured piece of silicon wafer as shown in FIGS. 3A–3D, extension tips according to the present invention may be formed from a variety of different materials. For example, thin metal wires, preformed whiskers of semiconductor material, carbon fibers, or metal may be used to form an extension tip. Thin film conductive structures, such as metal lines or contacts from an integrated circuit of, for example, a scrapped semiconductor device, may also provide a suitable material and structure for an extension tip. The metal lines or contacts may be removed from the integrated circuit by selectively etching, using a hydrofluoric-based etchant to remove oxide layers adhered to the metal lines or contacts, to cause the conductive traces to be isolated and removed from the semiconductor device. The metal lines or contacts may be made from tungsten or aluminum. A semiconductor material whisker, a metal whisker, a carbon fiber, an isolated metal line, or an isolated contact may be bonded to the lift-out probe 10 in the manner described with respect to the previous embodiments and, if necessary or desired, appropriately sized and shaped by ion milling with a FIB.

Figure 4A:
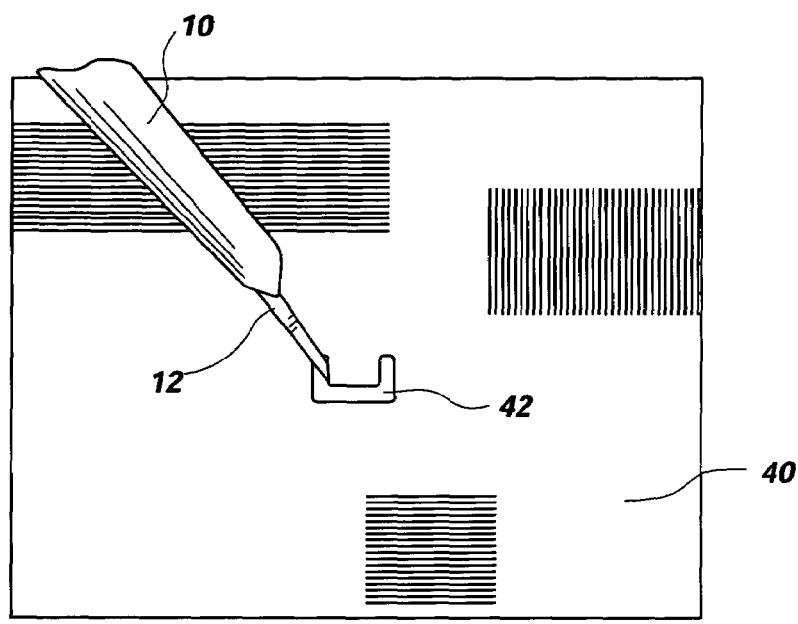
FIGS. 4A–4D are illustrations of employing a probe of the present invention to lift-out a specimen from an integrated circuit sample for further analysis.
Figure 4B:
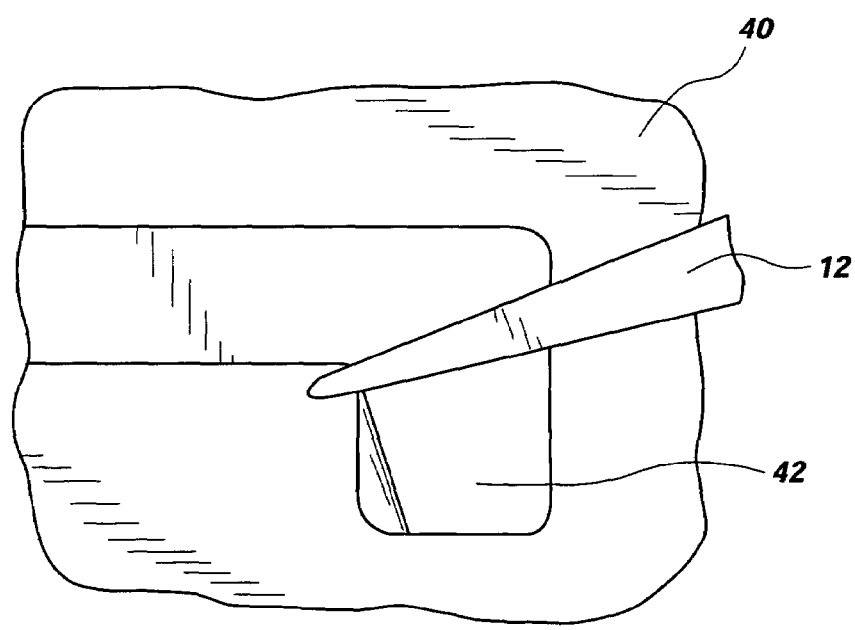
Figure 4C:
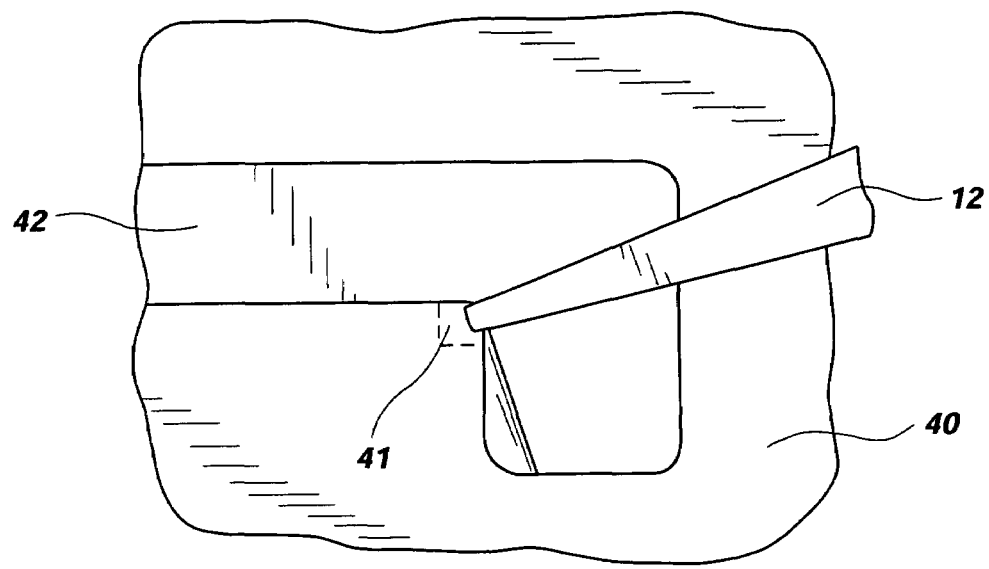
Figure 4D:
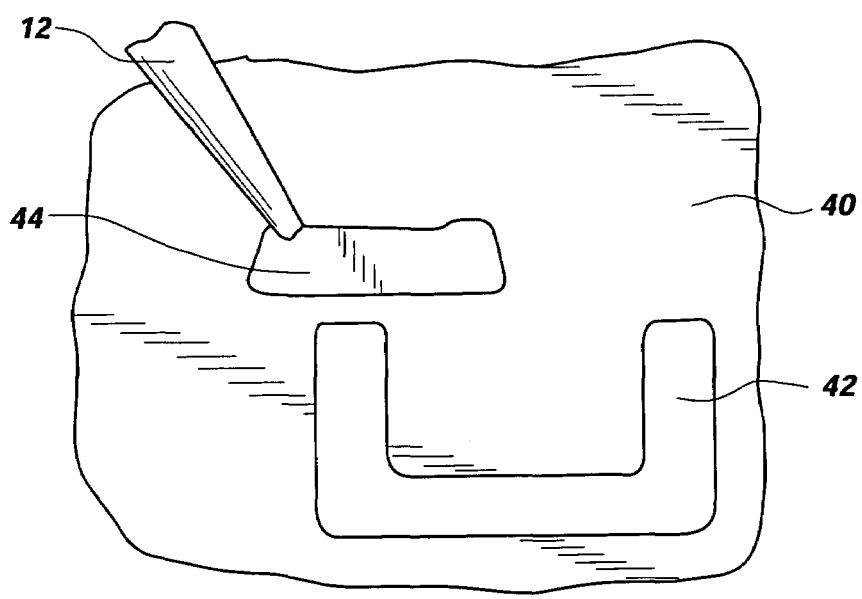
Figure 5:
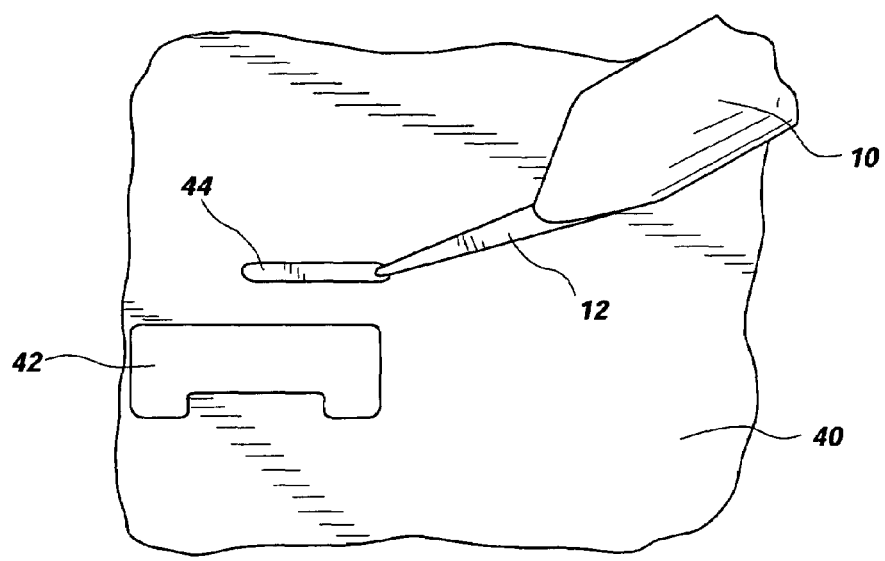
FIG. 5 is an illustration of an exemplary probe of the present invention shown bonded to a specimen that was removed from an integrated circuit sample.

The use of the probes of the present invention to remove a specimen from a larger sample is illustrated in FIGS. 4A–4D. First, a U-shaped trench 42 of a selected depth may be formed extending through a surface of a workpiece 40 by ion milling the workpiece (in this instance, an integrated circuit) at a desired location of a sample or specimen with a focused ion beam. As shown in FIG. 4B, the extension tip 12 of probe 26 (FIG. 2A) may be positioned using the probe controller 106 (FIG. 1) of a FIB system 102 (FIG. 1) to contact a desired sample location adjacent to the trench 42. Referring to FIG. 4C, an organometallic gas may be introduced into the FIB chamber 46 (FIG. 6) using the GIS of the FIB system 102 (FIG. 1) to the interface between the extension tip 12 and the workpiece 40. The interface may then be subjected to a controlled FIB to bond the extension tip 12 to the workpiece 40 at location 41 with, for example, platinum decomposed from the organometallic gas. As shown in FIG. 4D, the FIB may then be used to cut a specimen 44 from the workpiece 40 for subsequent removal from workpiece 40 and positioning for examination and analysis using the probe 26 (FIG. 2A). The specimen 44 may then be mounted onto a supporting medium. The FIB may then be used to sever the distal end of extension tip 12 from the specimen 44 and specimen 44 may be further thinned to a suitable thickness using ion milling to prepare it for examination with a TEM. FIG. 5 illustrates the size of the specimen 44 removed relative to lift-out probe 10, extension tip 12, and trench 42.

Figure 6:
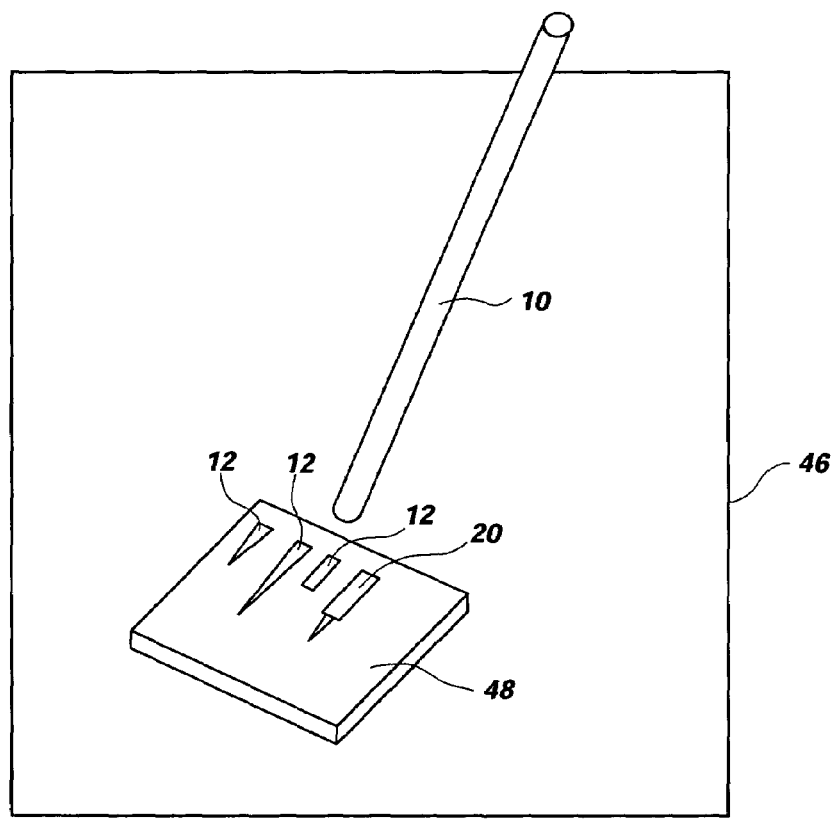
FIG. 6 illustrates a plurality of extension tips having various dimensions and geometries mounted on a support in a focused ion beam chamber.

The present invention also embraces forming a plurality of extension tips of various sizes and shapes that may be carried on a support in the FIB system. Referring to FIG. 6, a simplified illustration of a FIB chamber 46 is shown with the lift-out probe 10 located in the FIB chamber 46. A sample support 48 may be provided supporting a plurality of extension tips 12, 20, or both, of various sizes and geometries. The extension tips 12 or 20 may then be bonded to the lift-out probe 10 to form a probe 26 or a probe 28 (as illustrated in FIGS. 2A and 2B) in accordance with the present invention. By employing the extension tips, the useful life of the expensive lift-out probes 10 may be extended. A new extension tip may be attached when the old extension tip dulls or when a new extension tip having a specific size and shape is needed for a particular application. The present invention not only extends the useful life of lift-out probe 10, but eliminates the manufacturing costs associated with thinning a dull lift-out probe 10 or purchasing a new one.

The probes of the present invention, having extension tips with a small lateral dimension at their tip, enable controlled and accurate positioning thereof for landing on a desired location of a sample. The preparation of specimens is made easier and faster, and the likelihood of damaging a sample due to the contact force of the probe or undesired contact of the probe with a portion of the sample may be reduced. Therefore, the cost and turnaround time for preparing specimens using the FIB system may be significantly reduced. A smaller landing area at the intended sample location on a workpiece is needed relative to that required by conventional lift-out probes and particularly by worn probes, because of the small lateral dimensions of the extension tip, enabling removal of smaller specimens from the larger bulk sample and, thus, reducing the time required to bond the extension tip to the workpiece for sample removal and to subsequently thin the smaller samples taken from wafers for TEM structural analysis. The smaller extension tips are easier to control and monitor to achieve a precise location on the workpiece. Furthermore, the extension tips are relatively inexpensive to fabricate and may be easily detached and replaced, so that a new extension tip may be attached when dull or worn or if a different geometry or size of tip is desired. The probes of the present invention may also be employed in a variety of different applications, such as use as a micromechanical manipulator.

Although the foregoing description contains many specifics, these are not to be construed as limiting the scope of the present invention, but merely as providing certain exemplary embodiments. Similarly, other embodiments of the invention may be devised, which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A probe structure for use taking a sample from a larger body, the probe structure comprising:
   an elongated probe member sized and configured for use in a chamber of a focused ion beam system, the probe member having a front end region and a back end region; and
   an elongated extension tip having a proximal portion and a distal portion, the proximal portion being coupled to the front end region of the probe member.

2. The probe structure of claim 1, wherein the proximal portion of the elongated extension tip is bonded to the front end region of the elongated probe member with a mass of metal material.

3. The probe structure of claim 2, wherein the metal material is material decomposed from an organometallic precursor constituent.

4. The probe structure of claim 1, wherein the elongated extension tip comprises a semiconductor material.

5. The probe structure of claim 4, wherein the semiconductor material comprises single crystal silicon, single crystal germanium, or single crystal gallium arsenide.

6. The probe structure of claim 1, wherein the elongated extension tip comprises a segment of a thinned piece of semiconductor material.

7. The probe structure of claim 6, wherein the thinned piece of semiconductor material comprises single crystal silicon, single crystal germanium, or single crystal gallium arsenide.

8. The probe structure of claim 1, wherein the elongated extension tip comprises a metal or an alloy.

9. The probe structure of claim 1, wherein the elongated extension tip comprises a conductive thin film.

10. The probe structure of claim 1, wherein the elongated extension tip comprises a preformed whisker.

11. The probe structure of claim 1, wherein the elongated extension tip is of lesser lateral dimension than a lateral dimension of the front end region of the probe member.

12. The probe structure of claim 1, further comprising at least another elongated extension tip having a proximal portion and a distal portion, wherein the proximal portion of the at least another extension tip is bonded to the distal portion of the extension tip.

13. The probe structure of claim 1, wherein a longitudinal dimension of the elongated extension tip is greater than 1 $\mu$m.

14. The probe structure of claim 1, wherein a first lateral dimension of the elongated extension tip is between about 20 nm and about 2 $\mu$m.

15. The probe structure of claim 1, wherein the elongated extension tip comprises a tapered body having a second lateral dimension that tapers distally down to a first lateral dimension.

16. The probe structure of claim 1, wherein the probe member is a portion of a lift-out probe having a worn or damaged front end region.

17. The probe structure of claim 1, wherein the elongated extension tip is electrically conductive.

18. A method of fabricating a probe structure, comprising:
providing an elongated probe member sized and configured for use in a chamber of a focused ion beam system, and having a front end region defined by at least one lateral dimension and a back end region;
relatively positioning a portion of a body having a smaller lateral dimension than the at least one lateral dimension of the elongated probe member to contact the front end region thereof; and
bonding the front end region of the elongated probe member to the portion of the body.

19. The method according to claim 18, further comprising forming the body from a thinned piece of a semiconductor material.

20. The method according to claim 19, wherein the thinned piece of semiconductor material is formed by:
thinning a semiconductor substrate;
fracturing the semiconductor substrate into at least two pieces; and
ion milling one of the at least two pieces using a focused ion beam to form the portion of the body having the smaller lateral dimension.

21. The method according to claim 20, further comprising severing a portion of the thinned piece of a semiconductor material bonded to the elongated probe member to form an elongated extension tip.

22. The method according to claim 21, wherein the severing the portion of the thinned piece of semiconductor material is effected by directing the focused ion beam to cut the thinned piece of semiconductor material along a selected path to free the portion thereof bonded to the elongated probe member therefrom.

23. The method according to claim 22, wherein the bonding the front end region of the elongated probe member to the portion of the body comprises:
providing a precursor gas constituent at least proximate an interface between the front end region of the elongated probe member and the portion of the body; and
directing a focused ion beam to contact a portion of the precursor gas constituent proximate the interface to form a metal containing constituent extending between the elongated probe member and the portion of the body.

24. The method according to claim 18, wherein the bonding the front end region of the elongated probe member to the portion of the body comprises:
providing a precursor gas constituent at least proximate an interface between the front end region of the elongated probe member and the portion of the body; and
directing a focused ion beam to contact a portion of the precursor gas constituent proximate the interface to form a metal containing constituent extending between the elongated probe member and the portion of the body.

25. The method according to claim 18, further comprising selecting the body to be at least a portion of a conductive thin film structure from a semiconductor device.

26. The method according to claim 25, further comprising isolating the at least a portion of the conductive thin film structure from the semiconductor device by selectively etching a material of the semiconductor device proximate the at least a portion of the conductive thin film structure.

27. The method according to claim 25, further comprising at least one of sizing or shaping the at least a portion of the conductive thin film structure using a focused ion beam.

28. The method according to claim 27, wherein the bonding the front end region of the elongated probe member to the portion of the body comprises:
providing a precursor gas constituent at least proximate an interface between the front end region of the elongated probe member and the portion of the body; and
directing a focused ion beam to contact a portion of the precursor gas constituent proximate the interface to form a metal containing constituent extending between the elongated probe member and the portion of the body.

29. The method according to claim 18, further comprising ion milling the body along a selected path to form an extension tip.

30. The method according to claim 18, further comprising selecting the body to be a preformed whisker of a conductive material.

31. A method of fabricating a probe structure, comprising:
providing a plurality of extension tips of predetermined sizes and shapes, each extension tip of the plurality of extension tips having a proximal portion and a distal portion, inside a chamber of a focused ion beam system;
orienting a selected extension tip of the plurality of extension tips relative to a lift-out probe disposed within the chamber to contact the lift-out probe; and
bonding an end region of the lift-out probe to the proximal portion of the selected extension tip.

32. The method according to claim 31, wherein the bonding the end region of the lift-out probe to the proximal portion of the selected extension tip comprises:
depositing a precursor gas constituent at least proximate an interface between the end region of the lift-out probe and the proximal portion of the selected extension tip; and
directing a focused ion beam to contact a portion of the precursor gas constituent proximate the interface to form a metal-containing constituent extending between the lift-out probe and the proximal portion of the selected extension tip.

33. The method according to claim 31, further comprising severing at least a portion of the selected extension tip from the lift-out probe and bonding a proximal portion of another selected extension tip to the lift-out probe.

34. The method according to claim 31, further comprising bonding a proximal portion of another selected extension tip to the distal portion of the selected extension tip.

35. An analytical instrument comprising:
a focused ion beam system; and
a micromanipulator system comprising:
a probe controller operably coupled to a probe structure for accessing a chamber of the focused ion beam system, the probe structure comprising:
an elongated probe member having a front end region and a back end region; and
an elongated extension tip having a proximal portion and a distal portion coupled by the proximal portion to the front end region of the elongated probe member.

36. The analytical instrument of claim 35, wherein the proximal portion of the elongated extension tip is bonded to the front end region of the elongated probe member with a mass of metal material.

37. A method of taking a sample from a workpiece using a lift-out probe, comprising:

forming a lift-out probe structure including an elongated probe member sized and configured for use in a chamber of a focused ion beam system, and having an elongated extension tip bonded thereto;

contacting a workpiece with a distal end of the elongated extension tip;

bonding the distal end to the workpiece; and severing a portion of the workpiece bonded to the distal end from the workpiece.

38. The method of claim 37, further comprising severing the distal end of the elongated extension tip with the portion of the workpiece bonded thereto from the elongated extension tip.

* * * * *

UNITED STATES PATENT AND TRADEMARK OFFICE
CERTIFICATE OF CORRECTION

PATENT NO.         : 7,009,188 B2                                   Page 1 of 1
APPLICATION NO.    : 10/838878
DATED              : March 7, 2006
INVENTOR(S)        : Wang It is certified that error appears in the above-identified patent and that said Letters Patent is hereby corrected as shown below:

In column 9, line 7, in Claim 18, after "member" insert -- , --.

In column 9, line 8, in Claim 18, delete "focused ion beam" and insert -- Focused Ion Beam --, therefor.

In column 11, line 6, in Claim 37, after "member" insert -- , --.

In column 11, line 7, in Claim 37, delete "focused ion beam" and insert -- Focused Ion Beam --, therefor.

Signed and Sealed this

Eighth Day of April, 2008

JON W. DUDAS
*Director of the United States Patent and Trademark Office*